(12) United States Patent
Novikov et al.

(10) Patent No.: US 7,608,252 B2
(45) Date of Patent: Oct. 27, 2009

(54) SHAVE GEL COMPOSITION CONTAINING POLYGLYCERYL ESTER SURFACTANT

(75) Inventors: Alexander Novikov, Framingham, MA (US); Stephen H. Thong, Needham, MA (US)

(73) Assignee: The Gillette Company, Boston, MA (US)

( * ) Notice: Subject to any disclaimer, the term of this patent is extended or adjusted under 35 U.S.C. 154(b) by 1466 days.

(21) Appl. No.: 10/199,407

(22) Filed: Jul. 19, 2002

(65) Prior Publication Data

US 2004/0013633 A1 Jan. 22, 2004

(51) Int. Cl.
*A61K 7/15* (2006.01)
(52) U.S. Cl. .................. 424/73; 424/45; 424/47
(58) Field of Classification Search .................. 424/73, 424/70.31, 47, 45
See application file for complete search history.

(56) References Cited

U.S. PATENT DOCUMENTS

| 4,046,874 A | 9/1977 | Gabby et al. .................. 424/73 |
| 4,528,111 A | 7/1985 | Su ................................ 424/73 |
| 5,326,556 A | 7/1994 | Barnet et al. .................. 424/73 |
| 5,500,211 A | 3/1996 | George et al. ................. 424/73 |
| 5,925,364 A | 7/1999 | Ribier et al. ................. 424/410 |

FOREIGN PATENT DOCUMENTS

JP 04 234310 8/2004

OTHER PUBLICATIONS

Hatazaki, Yoichiro, (AN 2004:351627, HCAPLUS, abstract of JP 2004131425).*
Russo et al, Polyglycerol Esters, A New Class of Active Skin Moisturisers, Lonza 1997 (reprinted from Cosmetics and Toiletries). Formulating Personal Care Products With Polyglycerol Esters, Lonza Technical Bulletin, date unknown.

* cited by examiner

Primary Examiner—Sabiha N Qazi
(74) Attorney, Agent, or Firm—Ronald T. Sia; Andrew J. Hagerty

(57) ABSTRACT

Disclosed is a shaving composition in the form of a post-foaming gel that contains a polyglyceryl fatty ester surfactant. In particular the shaving composition comprises, in percent by weight, about 60% to about 93%, preferably about 70% to about 85%, water, about 2% to about 25%, preferably about 5% to about 20%, water dispersible (or soluble) surface active agent capable of forming a lather, about 1% to about 6%, preferably about 2% to about 5%, volatile post-foaming agent, and about 0.5% to about 5%, preferably about 1% to about 3%, polyglyceryl fatty ester surfactant.

12 Claims, No Drawings

SHAVE GEL COMPOSITION CONTAINING POLYGLYCERYL ESTER SURFACTANT

BACKGROUND OF THE INVENTION

The present invention relates to post-foaming shave gel compositions that contain a polyglyceryl fatty ester surfactant.

Currently, a widely used form of shaving preparation is the type referred to as a post-foaming shave gel. These post-foaming shave gels are now well-known and have been described, for example, in U.S. Pat. No. 2,995,521 (Bluard), U.S. Pat. No. 3,541,581 (Monson), U.S. Pat. No. 4,405,489 (Sisbarro), U.S. Pat. No. 4,528,111 (Su), U.S. Pat. No. 4,651,503 (Anderson), U.S. Pat. No. 5,248,495 (Patterson), U.S. Pat. No. 5,308,643 (Osipow), U.S. Pat. No. 5,326,556 (Barnet), U.S. Pat. No. 5,500,211 (George), U.S. Pat. No. 5,560,859 (Hartmann) and U.S. Pat. No. 5,858,343 (Szymczak). Such compositions generally take the form of an oil-in-water emulsion in which the post-foaming agent, generally a volatile (i.e., low boiling point) aliphatic hydrocarbon, is solubilized in the oil phase, and the water phase comprises a water-dispersible soap or interrupted soap component. The product is generally packaged in an aerosol container with a barrier, such as a piston or collapsible bag, to separate the post-foaming gel from the propellant required for expulsion of the product. The product is dispensed as a clear, translucent or opaque gel that is substantially free from foaming until it is spread over the skin, at which time it produces a foam lather generated by the volatilization of the volatile hydrocarbon foaming agent.

U.S. Pat. No. 4,046,874 (Gabby) discloses a soap-free aerosol shaving cream containing a polyglycerol fatty ester (e.g., triglycerol monostearate, decaglycerol distearate) and a water insoluble pulverulent bodying agent such as dextran, cellulose, talc, silica, sodium silicoaluminate and clay. However, such a product is not a shave gel and would not have good application aesthetics.

It would be highly desirable to provide a post-foaming shave gel composition that has excellent lubricity and emolliency without drying or irritating the skin, and without sacrificing any of the performance characteristics of conventional shave gels.

SUMMARY OF THE INVENTION

The present invention embraces a shaving composition in the form of a post-foaming gel that contains a polyglyceryl fatty ester surfactant. In particular the shaving composition comprises, in percent by weight, about 60% to about 93%, preferably about 70% to about 85%, water, about 2% to about 25%, preferably about 5% to about 20%, water dispersible (or soluble) surface active agent capable of forming a lather, about 1% to about 6%, preferably about 2% to about 5%, volatile post-foaming agent, and about 0.5% to about 5%, preferably about 1% to about 3%, polyglyceryl fatty ester surfactant.

DETAILED DESCRIPTION OF THE INVENTION

The term "fatty", as used herein, means a hydrocarbon chain having 12-22 carbon atoms ($C_{12-22}$). The chain may be straight or branched and may be saturated or unsaturated (typically one or two double bonds in the chain).

The polyglyceryl fatty ester surfactant provides a soft, moisturizing skin feel. Ideally, it will have an HLB of at least 9 or greater, preferably at least 10 or greater, more preferably at least 12 or greater. The polyglyceryl fatty ester surfactant has the formula

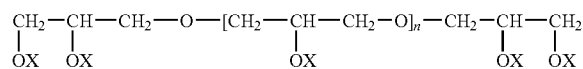

wherein n is 1 to 10, preferably 4 to 8, and

X is a hydrogen atom or a long chain acyl group (as defined below), provided that at least one X is a long chain acyl group, and preferably no more than three X's are long chain acyl groups. Most preferably no more than two X's are long chain acyl groups. The long chain acyl group may be derived from a $C_{12-22}$ fatty acid or an N-fatty acyl-neutral amino acid. (By the terminology the acyl group may be derived from a particular acid is meant simply that the OH group of the acid R—COOH is removed to yield the corresponding acyl group R—CO—.) Thus, the polyglyceryl fatty ester surfactant may be a polyglyceryl $C_{12-22}$ fatty acid ester or a polyglyceryl N-fatty acyl amino acid ester.

The long chain acyl group is preferably derived from a $C_{12-22}$ fatty acid. Thus, typical long chain acyl groups of this type include, for example, lauroyl, myristoyl, palmitoyl, stearoyl, isostearoyl, oleoyl, linoleoyl, and behenoyl. As mentioned above, the polyglyceryl ester will have at least one fatty acyl group, but preferably no more than three fatty acyl groups, in the molecule. Accordingly, when the acyl group is oleoyl, then the polyglyceryl ester will be named polyglyceryl-(n+2) (mono-, di- or tri-) oleate, where (n+2) is the degree of polymerization of the glycerol moiety (where n is as defined above) and is, thus, an integer from 3 to 12, preferably 6 to 10. Examples of suitable polyglyceryl fatty esters include, but are not limited to, polyglyceryl-10 oleate (also known as decaglycerol monooleate), polyglyceryl-6 stearate (also known as hexaglycerol monostearate), polyglyceryl-10 stearate (also known as decaglycerol monostearate), polyglyceryl-8 dipalmitate (also known as octaglycerol dipalmitate), polyglyceryl-10 dipalmitate (also known as decaglycerol dipalmitate), polyglyceryl-10 behenate (also known as decaglycerol monobehenate), and polyglyceryl-12 trilaurate (also known as dodecaglycerol trilaurate).

Alternatively, the long chain acyl group may also be derived from an N-fatty acyl-neutral amino acid. The fatty acyl moiety may be a $C_{12-22}$ fatty acyl group as described above (e.g., lauroyl, myristoyl, stearoyl, oleoyl, etc.). The neutral amino acid may be any short chain (i.e., 2 to 4 carbon atoms) amino acid such as glycine, alanine, β-alanine, aminobutyric acid, α-aminobutyric acid, N-methyl-β-alanine, and sarcosine. Sarcosine is preferred, in which case the long chain acyl group is N-fatty acyl-sarcosyl, and the polyglyceryl ester is a polyglyceryl N-fatty acyl-sarcosinate. Thus, suitable long chain acyl groups of this type include, for example, those derived from N-lauroyl-sarcosine, N-myristoyl-sarcosine, N-stearoyl-sarcosine, N-oleoyl-sarcosine, etc. Accordingly, examples of suitable polyglyceryl N-fatty acyl amino acid esters include, but are not limited to, polyglyceryl-10 N-stearoyl-sarcosinate (also known as decaglycerol mono-(N-stearoyl-sarcosinate)), polyglyceryl-10 N-lauroyl-sarcosinate (also known as decaglycerol mono-(N-lauroyl-sarcosinate)), polyglyceryl-8 di-(N-myristoyl-sarcosinate) (also known as octaglycerol di-(N-myristoyl-sarcosinate)), and polyglyceryl-12 tri-(N-lauroyl-sarcosinate) (also known as dodecaglycerol tri-(N-lauroyl-sarcosinate)).

The water dispersible surface active agent capable of forming a lather may comprise a soap, an interrupted soap, a detergent, an anionic surfactant, or a mixture of one or more of these. The soaps include, for example, the sodium, potassium and lower alkanolamine (preferably triethanolamine) salts of $C_{12-22}$, preferably $C_{12-18}$, fatty acids. Typical fatty acids include lauric, myristic, palmitic and stearic acid and mixtures thereof The preferred fatty acids are palmitic and stearic. The interrupted soaps include, for example, the sodium, potassium and lower alkanolamine (preferably triethanolamine) salts of N-fatty acyl sarcosines, wherein the fatty acyl moiety has 12 to 22, preferably 12 to 18, carbon atoms. Typical sarcosines include stearoyl sarcosine, myristoyl sarcosine, palmitoyl sarcosine, oleoyl sarcosine, lauroyl sarcosine, cocoyl sarcosine and mixtures thereof. The soaps and the interrupted soaps may be utilized in preneutralized form (i.e., as the sodium, potassium or alkanolamine salt) or in the free acid form followed by subsequent neutralization with sodium hydroxide, potassium hydroxide and/or lower alkanolamine (preferably triethanolamine). In any event, the final composition must contain sufficient base to neutralize or partially neutralize the soap component and adjust the pH to the desired level (typically between 5 and 8). It is most preferred that the compositions of the present invention include a soap.

The post-foaming agent may be any volatile hydrocarbon or halohydrocarbon with a sufficiently low boiling point that it will volatilize and foam the gel upon application to the skin, but not so low that it causes the gel to foam prematurely. The typical boiling point of such an agent generally falls within the range of –20° to 40° C. Preferred post-foaming agents are selected from saturated aliphatic hydrocarbons having 4 to 6 carbon atoms, such as n-pentane, isopentane, neopentane, n-butane, isobutane, and mixtures thereof. Most preferred is a mixture of isopentane and isobutane in a weight ratio (IP:IB) of about 1:1 to about 9:1, preferably about 2:1 to about 7:1, most preferably about 3:1. The post-foaming agent will normally be selected so as to provide a vapor pressure at 20° C. of about 3 to about 20 psig, preferably about 5 to about 15 psig. The post-foaming agent will be present in an amount to provide the shaving composition with a sufficiently rapid turnover—that is, transition from gel to foam when contacted with the skin—typically, in about 2 to about 30 seconds, preferably in about 5 to about 15 seconds.

Although not necessary to forming a useful shaving composition, other cosmetic ingredients may be advantageously added to improve the application aesthetics and/or achieve other shave benefits. For example, the composition may include one or more of the following components: beard wetting agents, skin conditioning agents (e.g., vitamins A, C and E, aloe, allantoin, panthenol, alpha-hydroxy acids, phospholipids, triglycerides, botanical oils, amino acids), foam boosters, emollients, humectants (e.g., glycerin, sorbitol, propylene glycol), fragrances, colorants, antioxidants, preservatives, etc.

The shaving composition may include a non-ionic and/or amphoteric surfactant, typically in an amount of about 1% to about 6%, preferably about 2% to about 5%, by weight. Suitable non-ionic surfactants include the polyoxyethylene ethers of fatty alcohols and vegetable oils (glycerides) and fatty amides, particularly the alkyl-substituted fatty amides. These surfactants will generally have about 6 to about 100, preferably about 20 to about 50, ethylene oxide units per molecule. Typical non-ionic surfactants include, for example, PEG-40 hydrogenated castor oil and Laureth-23. Suitable amphoteric surfactants include, for example, the betaines and sultaines such as cocoamidopropyl betaine, coco dimethyl carboxymethyl betaine, coco sultaine and the like.

It may be advantageous to include a sorbitan fatty ester or a sucrose fatty ester, typically in an amount of about 0.1% to about 3%, preferably about 0.3% to about 2%, by weight. These materials have multifunctional properties of emulsifier, moisturizer and anti-irritant. Sorbitan fatty esters include sorbitan stearate, sorbitan oleate, sorbitan isostearate, sorbitan laurate, sorbitan dioleate, etc. Sucrose fatty esters include sucrose stearate, sucrose oleate, sucrose isostearate, sucrose cocoate, sucrose distearate, etc. The sorbitan esters and sucrose esters may be mixtures of mono-, di- and tri-esters.

It may also be desirable to include an ester of a fatty acid and a fatty alcohol, wherein each fatty chain has from 12 to 22 carbon atoms, typically in an amount of about 0.5% to about 5%, preferably about 1% to about 3%, by weight. Preferably at least one of the fatty chains will be branched and at least one of the fatty chains will be unsaturated. Useful fatty esters include, for example, isostearyl linoleate, isocetyl oleate, isostearyl isostearate and isocetyl behenate. These materials provide both emolliency and lubrication.

It may further be desirable to include a propoxylated fatty amide, typically in an amount of about 0.5% to about 5%, preferably about 1% to about 3%, by weight. The propoxylated fatty amide will typically have from 1 to 3 propoxyl groups attached to a hydroxyloweralkyl fatty amide. Thus, suitable propoxylated fatty amides include, for example, PPG-2-hydroxyethyl coco/isostearamide, PPG-3-hydroxyethyl linoleamide, and PPG-2-hydroxyethyl cocamide.

The shave gel composition may include a water-soluble gelling aid or thickening agent to improve its consistency and stability, as well as to adjust its viscosity. These may include, for example, hydroxyalkyl cellulose polymers such as hydroxyethyl cellulose and hydroxypropyl cellulose (sold under the trademarks "Natrosol" and "Klucel" respectively), PEG-150 distearate, carboxymethyl cellulose, and cellulose methyl ether (sold under the trademark "Methocel"). The gelling aid or thickening agent is typically included in an amount of about 0.01% to 5%, preferably about 0.1% to 2%, by weight of the composition.

For increased lubricity, the shaving composition may include a lubricious water soluble polymer, typically in an amount of about 0.005% to about 2%, preferably about 0.01% to about 0.5%, by weight. Such polymers will typically have a molecular weight between about 300,000 and 15,000,000 daltons. Suitable polymers include, for example, polyvinylpyrrolidone, polyethylene oxide and polyacrylamide.

The shaving compositions of the present invention may be packaged in any suitable dispenser normally used for dispensing shaving gels. These include collapsible tubes, pump or squeeze containers, and aerosol-type dispensers with a barrier to separate the shaving composition from the propellant required for expulsion. The latter type of dispensers include: (1) mechanically pressurized bag-in-sleeve systems in which a thin-walled inner bag containing the product is surrounded by an outer elastic sleeve that is expanded during the product filling process and provides dispensing power to expel the product (e.g., the ATMOS System available commercially from the Exxel Container Co.); (2) manually activated air pump spray devices in which a pump system is integrated into the container to allow the user to pressurize the container with air in order to expel the product (e.g., the "AIRSPRAY" system available from Airspray International); (3) piston barrier systems in which the product is separated from the driving means by a tight-fitting piston which seals to the side of the container and may be driven by a spring under tension, by a vacuum on the product side of the piston, by finger pressure, by gas pressure to the piston, or by a variety of other means known to the packaging industry; and (4) bag-in-can (SEPRO) systems in which the product is contained in a flexible bag within a can, with a suitable propellant injected into the space between the can and the flexible bag. It is preferred to protect the composition from oxidation and heavy metal contamination. This can be achieved, for example, by purging the composition and container with nitrogen to remove oxygen and by utilizing inert containers (e.g., plastic bottles or bags, aluminum cans or polymer coated or lined cans).

The invention may be further described by the following examples in which all parts and percentages are by weight.

Examples 1-4-Post-Foaming Shave Gel

| Ingredient | Weight Percent | | | |
|---|---|---|---|---|
| | Ex. 1 | Ex. 2 | Ex. 3 | Ex. 4 |
| Triethanolamine | 5.00 | 5.00 | 5.00 | 5.00 |
| Palmitic acid | 4.13 | 4.13 | 4.13 | 4.13 |
| Stearic acid | 4.04 | 4.04 | 4.04 | 4.04 |
| Polyglyceryl-10 Oleate | 1.44 | | 1.44 | |
| Polyglyceryl-10 Dipalmitate | | 1.44 | | 1.44 |
| Isopentane/isobutane (3:1) | 3.85 | 3.85 | 3.85 | 3.85 |
| PEG-40 Hydrogenated Castor Oil | 3.85 | 3.85 | 3.85 | 3.85 |
| PPG-2 Hydroxyethyl Cocamide | 1.92 | 1.92 | | |
| PPG-3 Hydroxyethyl Linoleamide | | | 1.92 | 1.92 |
| Isostearyl linoleate | 1.92 | | 1.92 | |
| Isostearyl isostearate | | 1.92 | | 1.92 |
| Sucrose stearate | 0.48 | 0.48 | | |
| Sorbitan laurate | | | 0.48 | 0.48 |
| Hydroxyethyl cellulose | 0.29 | 0.29 | 0.29 | 0.29 |
| Fragrance | 0.77 | 0.77 | 0.77 | 0.77 |
| Preservative/Antioxidant | 0.03 | 0.03 | 0.03 | 0.03 |
| Polyox Coagulant | | 0.01 | | 0.01 |
| Polyacrylamide | 0.01 | | 0.01 | |
| Water | 72.27 | 72.27 | 72.27 | 72.27 |

The above-described compositions are made in the following manner: The water soluble components (e.g., the polymers) are added to water and mixed until the polymers are completely dissolved (about 30 min.). The aqueous mixture is then heated and the fatty acids are added at about 60° C. and well mixed while the heating continues. At 80-85° C. the triethanolamine is added and mixed for about 30 minutes to form the aqueous soap phase. The oil phase components (i.e., Polyglyceryl-10 oleate, PEG-40 hydrogenated castor oil, PPG-2 hydroxyethyl cocamide, isostearyl linoleate, sucrose stearate) are separately mixed and melted, then added to the aqueous soap phase at about 75-80° C. and mixed for about 30 minutes. While cooling this emulsion, the remaining ingredients (e.g., dye, fragrance, antioxidant, preservative) are added below about 40° C. and mixed well. The concentrate (at about 30° C.) is then combined with the volatile post-foaming agent within the filling line and filled into bottom-gassed aerosol cans through the valve under nitrogen pressure.

While particular embodiments of the invention have been shown and described for illustrative purposes, it will be apparent to those skilled in the art that various changes and modifications may be made without departing from the spirit and scope of the invention, which is defined by the claims which follow.

What is claimed is:

1. A shaving composition in the form of a post-foaming gel comprising, in percent by weight, about 60% to about 93% water, about 2% to about 25% water dispersible surface active agent capable of forming a lather, about 2% to about 5% volatile post-foaming agent, and 0.5% to 5% polyglyceryl fatty ester surfactant, wherein the polyglyceryl fatty ester surfactant has the formula

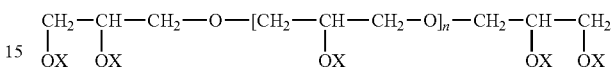

wherein n is 4 to 10, and X is a hydrogen atom or a long chain acyl group derived from a $C_{12-22}$ fatty acid or an N-fatty acyl-neutral amino acid, provided that at least one X is a long chain acyl group and no more than three X's are long chain acyl groups.

2. The shaving composition of claim 1 wherein the polyglyceryl fatty ester surfactant comprises a polyglyceryl $C_{12-22}$ fatty acid ester or a polyglyceryl N-fatty acyl aminoacid ester.

3. The shaving composition of claim 1 wherein, with respect to the polyglyceryl fatty ester surfactant, the long chain acyl group is derived from a $C_{12-22}$ fatty acid.

4. The shaving composition of claim 1 wherein, with respect to the polyglyceryl fatty ester surfactant, the long chain acyl group is selected from lauroyl, myristoyl, palmitoyl, stearoyl, isostearoyl, oleoyl, linoleoyl, and behenoyl.

5. The shaving composition of claim 1 wherein, with respect to the polyglyceryl fatty ester surfactant, the long chain acyl group is derived from an N-fatty acyl-neutral amino acid wherein the neutral amino acid is selected from glycine, alanine, βalanine, aminobutyric acid, αaminobutyric acid, N-methyl-β-alanine, and sarcosine.

6. The shaving composition of claim 5 wherein, with respect to the polyglyceryl fatty ester surfactant, the long chain acyl group is N-fatty acyl-sarcosyl.

7. The shaving composition of claim 1, 3, 4, 5 or 6 wherein, with respect to the polyglyceryl fatty eater surfactant, n is 4 to 8 and no more than two X's are long chain acyl groups.

8. The shaving composition of claim 1 wherein the polyglyceryl fatty ester surfactant has an HLB of at least 10 greater.

9. The shaving composition of claim where the polyglyceryl fatty ester surfactant comprises polyglyceryl-10 oleate.

10. The shaving composition of claim 1, 3, 4 or 9 wherein the composition comprises, in percent by weight, about 70% to about 85% water, about 5% to about 20% water dispersible surface active agent capable of forming a lather, about 2% to about 5% volatile post-foaming agent, and about 1% to about 3% of a polyglyceryl fatty ester surfactant.

11. The shaving composition of claim 10 wherein the water dispersible surface active agent comprises a soap.

12. The shaving composition of claim 1, 3, 4 or 9 additionally comprising one or more materials selected from the group consisting of a sorbitan fatty ester, a sucrose fatty ester, an ester of a fatty acid and a fatty alcohol, and a propoxylated fatty amide.

* * * * *

UNITED STATES PATENT AND TRADEMARK OFFICE
CERTIFICATE OF CORRECTION

PATENT NO.       : 7,608,252 B2           Page 1 of 1
APPLICATION NO. : 10/199407
DATED            : October 27, 2009
INVENTOR(S)      : Novikov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1473 days.

Signed and Sealed this

Twelfth Day of October, 2010

David J. Kappos
*Director of the United States Patent and Trademark Office*